United States Patent [19]
Kunii et al.

[11] 4,282,879
[45] Aug. 11, 1981

[54] ULTRASONIC DIAGNOSING APPARATUS

[75] Inventors: Yutaka Kunii; Toshikuni Shimoji; Masaaki Tsutsumi, all of Kawasaki, Japan

[73] Assignee: Tokyo Shibaura Denki Kabushiki Kaisha, Japan

[21] Appl. No.: 13,975

[22] Filed: Feb. 22, 1979

[30] Foreign Application Priority Data

Feb. 23, 1978 [JP] Japan .................................. 53/20271

[51] Int. Cl.³ ............................................... A61B 5/00
[52] U.S. Cl. ...................................... 128/660; 73/621
[58] Field of Search ............................... 128/660–663; 73/618–625

[56] References Cited

U.S. PATENT DOCUMENTS

| | | | |
|---|---|---|---|
| 3,425,507 | 2/1969 | Caldwell et al. | 73/624 |
| 3,955,561 | 5/1976 | Eggleton | 128/661 |
| 4,120,291 | 10/1978 | Paton et al. | 128/660 |
| 4,130,022 | 12/1978 | Goodrich et al. | 128/660 |
| 4,151,834 | 5/1979 | Sato et al. | 128/660 |

Primary Examiner—William E. Kamm
Attorney, Agent, or Firm—Finnegan, Henderson, Farabow, Garrett & Dunner

[57] ABSTRACT

An ultrasonic diagnosing apparatus comprises a first mechanism connected to the rotation shaft of a motor to convert a rotation motion to a circular motion, and an universal joint type second mechanism connecting at one end to said first mechanism such that it can be freely moved in any direction. The universal joint type second mechanism is connected at the other end such that it can swing in a predetermined direction to cause the circular motion transmitted by said first mechanism to be converted to the circular motion to permit an ultrasonic probe to oscillatingly scan a subject to be examined.

11 Claims, 4 Drawing Figures

ULTRASONIC DIAGNOSING APPARATUS

BACKGROUND OF THE INVENTION

This invention relates to an ultrasonic diagnosing apparatus including an improved high-speed sector scanner adapted to effect a high-speed sector scan by an ultrasonic probe.

When a tomographic image corresponding to the human heart is obtained, during the transmission of ultrasonic waves the presence of the ribs of a human being tend to block the transmission of some of the ultrasonic waves. In order to prevent such an influence from the ribs, a method for scanning often includes bringing an ultrasonic probe (a device for transmitting and receiving ultrasonic waves to obtain ultrasonic echoes) into the closest possible proximity to the body surface of a human being and effecting scanning so as to send ultrasonic pulses from a position between the ribs.

In order to transmit ultrasonic pulses from a position between the ribs toward the heart of the human being, it is very effective to effect a sector scanning by an ultrasonic probe, by rotating the probe in a sector fashion. Sector scanning is effective because that the inter-rib spacing is very narrow. Since the human heart is constantly pulsated, no good-quality tomographic image corresponding to the heart can be obtained unless ultrasonic echoes are captured through high-speed sector scanning.

Conventionally, an ultrasonic high-speed sector scanner for effecting a high-speed sector scanning has been used.

FIG. 1 is a schematic diagram showing a conventional scanner. Reference numeral 1 shows a shaft. At both end portions the shaft 1 is supported by corresponding bearings 2, 2'. The number 3 shows a probe holder mounted on the shaft 1, and an ultrasonic probe 4 is held by the probe holder 3. The number 5 shows a pulley fixedly mounted on the shaft 1. The number 6 shows a motor; 7 shows a drive side pulley connected to the motor 6 so that it is rotatably driven; 8 shows a belt run between the drive side pulley 7 and the pulley 5; and 9 shows a bearing. The motor 6 is forwardly and reversely rotated in a repetitive fashion. Since the pulley 7 is mounted on the shaft of the motor and the belt 8 is run between the pulley 7 and the pulley 5, the shaft 1 can be forwardly and reversely rotated through such a mechanism. The ultrasonic probe 4, mounted on the probe holder 3 which is on the shaft 1, effects an oscillating movement to effect a sector-scanning.

The above-mentioned apparatus effects a sector scanning through the forward and reverse rotation of the motor 6, thus providing a bar to the obtainment of a high-speed apparatus. Furthermore, the motor requires a great torque, making the apparatus bulky as a whole.

When ultrasonic pulses are emitted from a position between the ribs toward the heart of the human being, the ultrasonic wave transmit/receive surface of a container including a sector scanner (FIG. 1) and ultrasonic wave transmitting medium has to be contacted with an inter-rib surface portion of the human body. Furthermore, the apparatus including such a container needs to be made compact and light in weight.

Another apparatus is also known which is adapted to convert the rotational motion of a motor to a repetitive, rotational motion so as to obtain a sector movement. Such an apparatus lacks the smoothness of conversion to the repetitive, rotational movement, making it difficult to obtain a greater sector angle (an oscillation angle of the ultrasonic probe). Moreover, it is also difficult to detect the position corresponding to a scanning angle required for the presentation of an image. Thus, it would be difficult to correctly display an ultrasonic tomographic image, as well as to adjust the sector angle.

The adjustment of the sector angle of the ultrasonic probe is very important in obtaining a tomographing heart image. For example, if the number of tomographic images as displayed during one second is fixed, the number of scanning lines corresponding to one tomographic image does not vary for a greater sector angle, because the speed of the ultrasonic wave is fixed. Thus, a very coarse image is displayed on the screen of a monitor device. If, on the other hand, the sector angle is smaller, a fine, good-quality tomographic image can be obtained. When, however, scanning is started at a smaller sector angle, only one portion of the heart of the human being is displayed as an image, and it would be difficult to locate that heart region required for diagnosis. It would be also difficult to associate this region with other regions. In order to quickly locate a region of interest (ROI) of the heart for effective diagnosis, it is necessary to observe a wider range of image at a wider sector angle, to quickly and accurately locate the ROI of the heart from the overall point of view. It is then necessary to obtain a good-quality image, at a narrow sector angle, which corresponds to only the ROI of the heart. In the conventional apparatus it would be difficult to adjust the sector angle at will.

SUMMARY OF THE INVENTION

According to this invention there is provided an ultrasonic diagnosing apparatus comprising a swinging angle adjusting slider mounted on a rotation shaft of a motor to permit it to be slidably moved, a tunning fork-like support arm, an ultrasonic probe held at an intersection of support shafts orthogonal to each other, one of said support shafts being held in a predetermined position in a plane including the axis of said rotation shaft, the other support shaft being journaled on the opposite sides of one end portion of said tunning fork-like support arm, a spherical bearing mounted on the base end of said tunning fork-like support arm, and a connecting rod having one end supported on the slider and the other end connected to the spherical bearing so that a rotation force of the motor can be transmitted, in which an angle between the connecting rod and the support arm can be adjusted by the slider, the rotation motion of the motor can be converted by the connecting rod to a circular motion, and the circular motion is smoothly converted by the support shaft to an oscillatory motion.

DETAILED DESCRIPTION OF THE INVENTION

Figure 1:
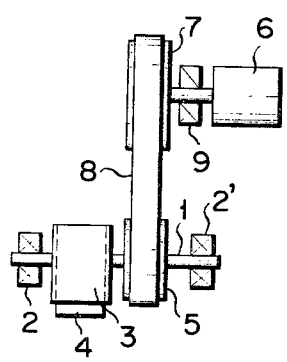
FIG. 1 is a front view showing a conventional ultrasonic diagnosing apparatus.
Figure 2:
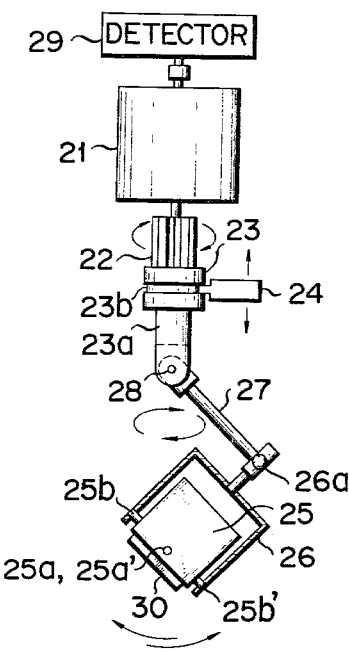
FIG. 2 is a front view showing an ultrasonic diagnosing apparatus according to an embodiment of this invention.

FIG. 2 is a front view showing the construction of a sector scanner section according to one embodiment of this invention.

In FIG. 2, reference numeral 21 shows a motor through which a rotating shaft extends. A shaft 22 is secured to one end of the rotating shaft of the motor 21 and has longitudinally parallel grooves and a cylindrical slider 23 is fitted over the shaft 22 and can be moved londitudinally of the shaft 22 such that it is guided along the grooves of the shaft 22. A cylindrical body 23a is formed on one side of the slider 23 such that it is coaxial with the shaft 22. When the slider 23 is moved longitudinally along the shaft 22, the position of the forward end of the cylindrical body 23a is varied. In the outer peripheral portion of the slider 23 a guide groove 23b is formed in a direction perpendicular to the shaft 22. 24 shows an operation lever having its forward end brought into engagement with the guide groove 23b. The operation lever 24 is adapted to position the slider 23. The reference number 25 shows a probe holder. Four support shafts 25a, 25a' and 25b, 25b' are provided on the probe holder 25 such that they are perpendicular to the center axis of the probe holder 25 and such that they are arranged two on one line and two on another line which is orthogonal to said one line. The pair of support shafts 25a, 25a' are each held in a bearing, not shown, which is provided in proper position on a plane including the center line of the shaft 22. Another pair of support shafts 25b, 25b' are swingably held on the opposite ends of one end portion of a tuning fork-like support arm 26. A spherical bearing 26a is formed on the base of the support bracket 26 and a connecting rod 27 is connected at one end to the spherical bearing 26a. The other end of the connecting rod 27 is swingably connected to the forward end of the cylindrical body 23a of the slider 23 by a shaft 28 which is parallel with the axis of the support shafts 25a, 25a'. Reference numeral 29 shows a position detector for rotation angle detection, which is connected to a shaft at the other end of the motor 21. 30 shows an ultrasonic probe which is held on the probe holder 25.

The apparatus of this invention will be operated as follows:

At first, the operation lever 24 is fixed in a desired position to position the slider 23. When the motor 21 is rotated the rotation force is transmitted through the shaft 22 to the slider 23. Since the operation lever 24 is held in position with its forward end contacted with the guide groove 23b of the slider 23, the slider 23 is rotated, while holding the position determined by the operating lever 24. The connecting rod 27 connected to the support arm 26 is connected by the shaft 28 and thus rotated by the rotation of the slider 23. The support arm 26 can be freely moved, in any direction, through the spherical bearing 26a. The probe holder 25 is supported by the support shafts 25a, 25a' and connected by the support shafts 25b, 25b' to the support arm 26, thus serving as a universal joint. If the support arm is at a certain angle to the connecting rod 27 as shown in FIG. 2, the connection between the connecting rod 27 and support arm 26 is rotated by the rotation of the slider 23 such that it describes a circle. Possible torsion of the connecting rod 27 as involved during the circular movement is eliminated due to the presence of the spherical bearing 26a. Forward and rearward forces (FIG. 2) involved during the circular movement of the connection between the connecting rod 27 and the probe holder 26 are released by the support arm 26 and the support shafts 25b, 25b' on the probe holder 25, and only the leftward and rightward forces act on the probe holder 25. Consequently, with the rotation of the motor 21 the probe holder 25 swings in the leftward and rightward directions with the support shafts 25a, 25a' serving as a swinging center, and the acoustic probe 30 held on the probe holder 25 swings and oscillates with the result that a section scanning can be effected by an ultrasonic wave emitted from the ultrasonic wave probe 30.

Since the position detector 29 is connected directly to the motor 21, the rotation position of the motor 21 is detected. By the detection signal the corresponding action is taken with respect to the display position of an ultrasonic image.

When the operating lever 24 is moved upwardly, the slider 23 engaged by the operating lever 24 is moved upwardly and the distance between the support shafts 25a, 25a' of the probe holder 25 and forward end of the cylindrical body 23 of the slider 23 is thus lengthened. Since the connecting rod 27 is pulled upwardly, an angle between the connecting rod 27 and the axis of the support arm 26 is made greater and thus the oscillation angle of the probe holder 25 is made smaller. When, on the other hand, the operating lever 24 is moved downwardly, the distance between the support shafts 25a, 25a' and the forward end of the cylindrical body 23a of the slider 23 is made smaller and thus an angle between the connecting rod 27 and the support arm 26 is made smaller. As a result, the inclination of the probe holder 25 is made greater and the oscillation angle of the probe holder 25 is made greater.

The oscillation angle of the probe holder 25 can be properly varied by the position of the operating lever 24. If an amount of movement is detected, the sector angle (oscillation angle) can be calculated and the present direction of the probe holder 25 can be obtained based on such an amount of movement and rotation position of the motor 21.

Figure 3:
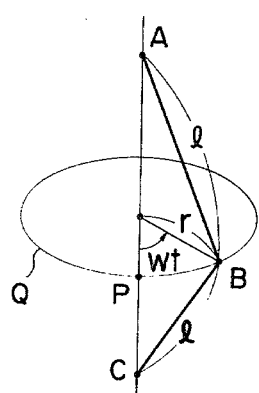
FIG. 3 is a view showing the mode of motion of the parts of the apparatus of this invention.

The position detection of the ultrasonic probe 30 which is important for the display of an ultrasonic image will be explained below by referring to FIGS. 3 and 4. FIG. 3 is a diagram showing the mode of motion of the parts of the apparatus of this invention.

In FIG. 3 the point A shows the shaft 28 where the cylindrical body 23a and connecting rod 27 are connected, the point B shows the position of a center of rotation of the spherical bearing 26a where the support arm 26 and connecting rod 27 are connected, and the point C shows the position of the support shafts 25a, 25a' of the probe holder 25. In FIG. 3, Q shows the locus of the point B which is present in one plane. The center of the plane, O, as defined by said locus lies on a straight line connecting the points A and C, and the point P shows a base point of the point B. FIG. 3 shows positional relation taken after t seconds. In FIG. 3 it is supposed that segments AB and BC have an equal length of l.

Figure 4:
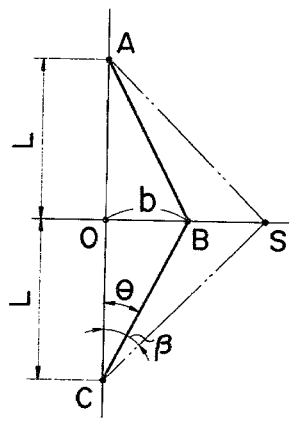
FIG. 4 is a view showing the mode of motion as represented in one plane.

In FIG. 4 the positional relation of FIG. 3 is expressed in one plane. In FIG. 4, b shows a distance OB and the point S shows the rotation position of the point B which satisfies a relation:

$$\omega t = \pi/4 \text{ (radian)}$$

where $\omega t$ denotes the angular velocity of the motor.

From these it follows that the equation of motion of the ultrasonic probe is:

$$\tan \theta = \frac{b}{L} = \frac{l \sin \beta \sin \omega t}{l \cos \beta} \quad (1)$$
$$= \tan \beta \sin \omega t$$
$$\theta = \tan^{-1}(\tan \beta \sin \omega t) \quad (2)$$

where
$\theta$: the inclination angle of the ultrasonic probe
$\beta$: a maximum angle corresponding to $\frac{1}{2}$ of the sector angle Thus, the inclination angle $\theta$ of the ultrasonic probe can be obtained from Equation (2).

The adjustment of the sector angle, which is one of the features of this invention, will be explained below.

From FIGS. 3 and 4, $\tan \beta$ of Equation (1) can be expressed as follows:

$$\tan \beta = \frac{\overline{OS}}{\overline{OC}} = \frac{r}{L} = \frac{\sqrt{l^2 - L^2}}{L} \quad (3)$$

When a segment $\overline{AC}$ varies an amount $\Delta L$, $$\tan \beta = \frac{\sqrt{l^2 - \left(L + \frac{\Delta l}{2}\right)^2}}{L + \frac{\Delta L}{2}} = \sqrt{\frac{l^2}{\left(L + \frac{\Delta L}{2}\right)^2}} \quad (4)$$

Thus, $\beta$, $\frac{1}{2}$ of the sector angle, varies as in Equation (4).

Substituting Equation (4) into Equation (1) yields an equation of motion at that time.

According to this invention the inclination angle of the ultrasonic probe can be detected with high accuracy and the sector angle can be easily adjusted to $2\beta$.

According to this invention there is provided an ultrasonic diagnosing apparatus comprising a slider slidably mounted on a rotation shaft of a motor to permit it to be rotated along the longitudinal direction of the rotation shaft, a tuning fork-like support arm, an ultrasonic probe held at an intersection of support shafts orthogonal to each other, one of the support shafts being held in a predetermined position in a plane including the axis of the rotation shaft, the other support shaft being journaled on one end portion of the opposite sides of the tuning fork-like support arm, a spherical bearing mounted on the base end of the support arm, and a connecting rod having one end supported on the slider and the other end connected to the spherical bearing, in which the rotation of the motor is converted by the connecting rod to a circular motion, those components of the circular motion which are orthogonal to the rotation direction of said one support shaft are absorbed by the support arm, and only motion components present in the rotation direction of said one support shaft are transmitted to the ultrasonic probe to permit the latter to smoothly oscillate with the support shaft as a center. The ultrasonic diagnosing apparatus of this invention has the following advantages:

(1) Since the rotation of the motor is only in one direction, a small-torque motor can be used;

(2) An angle between the connecting rod and the support arm can be properly adjusted by adjustably moving the slider. Thus, the oscillation angle of the probe can be freely adjusted in a wider range.

(3) The oscillation angle and present position of the ultrasonic probe can be easily and accurately detected due to such a geometric configuration.

The connecting rod and slider may be formed integral with each other so that a fixed angle can be used. In this case, a desired sector angle can be obtained by exchanging one such combination for another.

What we claim is:

1. An apparatus for oscillating an ultrasonic probe of an ultrasonic sector scanner through a variable sector angle to sector scan a subject to be examined comprising:
    a holder for supporting the ultrasonic probe,
    means pivotably mounting said holder about a first fixed axis to sector scan the probe about said first fixed axis,
    a support member pivotably fixed to said holder about a second axis substantially perpendicular to said first fixed axis, thereby forming in effect a universal joint,
    a connecting rod,
    a spherical bearing joining one end of said connecting rod to said support member at a point on said support member spaced from said first fixed axis,
    an adjustment mechanism rotatable about a third fixed axis and pivotably fixed to the end of said connecting rod at a pivot point opposite said spherical bearing, said adjustment mechanism being slidable along said third fixed axis to vary the distance between said pivot point and said first fixed axis, whereby the probe will oscillate through a sector angle as the adjustment mechanism rotates and whereby the sector angle traveled by the probe is a function of the distance between said first fixed axis and said pivot point, and
    means for sliding said adjustment mechanism along said third fixed axis to thereby adjust the sector angle through which said holder oscillates.

2. The ultrasonic scanner of claim 1 further comprising a drive shaft rotatable about said third fixed axis and wherein said adjustment mechanism includes:
    an elongated member fixed to said drive shaft, said elongated member having a longitudinal groove parallel to the axis of said drive shaft, and
    a cylindrical member pivotably fixed to said connection rod, said cylindrical member being slidable on said elongated member and having a tooth engaging and slidable within the longitudinal groove of said elongated member.

3. The ultrasonic scanner of claim 2 further comprising an operation lever connected to said cylindrical member for effecting the sliding of said cylindrical member on said elongated member.

4. The ultrasonic scanner of claim 3 wherein a groove is formed in said cylindrical member and said operation lever rides in said groove.

5. The ultrasonic axis of claim 2 wherein said first fixed axis and said second axis are perpendicular to the axis of said drive shaft.

6. The ultrasonic scanner of claim 5 wherein said second axis intersects said first fixed axis.

7. The ultrasonic axis of claim 6 wherein said first fixed axis and said second axis intersect at a point on the axis of said drive shaft.

8. The ultrasonic apparatus of claim 5 wherein said first fixed axis intersects with the axis of said drive shaft, and the connection rod is pivotably fixed to said cylindrical member at a point on the axis of said drive shaft.

9. The ultrasonic scanner of claim 8 wherein a pair of pins are fixed to the exterior of said holder along said second axis and said support member includes a first arm pivotably connected to one of said pins and a second arm pivotably connected to said other pin.

10. The ultrasonic scanner of claim 9 further comprising a position detector coupled with said drive shaft for detecting the rotation angle of said drive shaft.

11. The ultrasonic scanner of claim 10 further comprising a drive motor connected to said rotatable drive shaft.

* * * * *

UNITED STATES PATENT AND TRADEMARK OFFICE
CERTIFICATE OF CORRECTION

PATENT NO. : 4,282,879
DATED : August 11, 1981
INVENTOR(S) : YUTAKA KUNII ET AL

It is certified that error appears in the above—identified patent and that said Letters Patent is hereby corrected as shown below:

Column 5, line 1, replace "velocity" with -- displacement --.

Signed and Sealed this

First Day of June 1982

[SEAL]

Attest:

GERALD J. MOSSINGHOFF

Attesting Officer     Commissioner of Patents and Trademarks